(12) United States Patent
Sarpen et al.

(10) Patent No.: US 9,169,439 B2
(45) Date of Patent: Oct. 27, 2015

(54) METHOD AND APPARATUS FOR TESTING COAL COKING PROPERTIES

(75) Inventors: Jacob P. Sarpen, Chicago, IL (US); John F. Quanci, Haddonfield, NJ (US); Mark A. Ball, Richlands, VA (US); Paul J. Norton, Media, PA (US); Roy J. Griffey, Grundy, VA (US); Jose Eustaquio DaSilva, Espirito Santo (BR)

(73) Assignee: SUNCOKE TECHNOLOGY AND DEVELOPMENT LLC, Lisle, IL (US)

( * ) Notice: Subject to any disclaimer, the term of this patent is extended or adjusted under 35 U.S.C. 154(b) by 367 days.

(21) Appl. No.: 13/598,394

(22) Filed: Aug. 29, 2012

(65) Prior Publication Data

US 2014/0061018 A1     Mar. 6, 2014

(51) Int. Cl.
| | | |
|---|---|---|
| *C10B 45/00* | (2006.01) | |
| *G01N 33/22* | (2006.01) | |
| *C10B 53/00* | (2006.01) | |
| *C10B 57/00* | (2006.01) | |
| *G01N 30/12* | (2006.01) | |

(52) U.S. Cl.
CPC ............... *C10B 45/00* (2013.01); *C10B 53/00* (2013.01); *C10B 57/00* (2013.01); *G01N 33/222* (2013.01); *G01N 2030/125* (2013.01)

(58) Field of Classification Search
CPC .......... G01N 33/222; G01N 2030/125; C10B 45/00; C10B 53/00; C10B 57/00
USPC ........................................ 201/1, 41; 436/155
See application file for complete search history.

(56) References Cited

U.S. PATENT DOCUMENTS

| | | | |
|---|---|---|---|
| 469,868 | A | 3/1892 | Osbourn |
| 1,424,777 | A | 8/1922 | Schondeling |
| 1,430,027 | A | 9/1922 | Plantinga |
| 1,486,401 | A | 3/1924 | Van Ackeren |
| 1,572,391 | A * | 2/1926 | Klaiber .......................... 374/46 |
| 1,721,813 | A * | 7/1929 | Geipert ......................... 436/155 |

(Continued)

FOREIGN PATENT DOCUMENTS

| | | |
|---|---|---|
| CA | 2775992 A1 | 5/2011 |
| CN | 2064363 U | 10/1990 |

(Continued)

OTHER PUBLICATIONS

ASTM D5341-99(2010)e1, Standard Test Method for Measuring Coke Reactivity Index (CRI) and Coke Strength After Reaction (CSR), ASTM International, West Conshohocken, PA, 2010.*

(Continued)

*Primary Examiner* — In Suk Bullock
*Assistant Examiner* — Jonathan Miller
(74) *Attorney, Agent, or Firm* — Perkins Coie LLP

(57) ABSTRACT

A method of testing the coking qualities of sample quantities of coal in a test container and the structure of the test container are disclosed. A test container which is ideally reusable is adapted to receive one or more samples of coal to be tested and then the test container is inserted into a coking oven along with additional, conventional coal during a conventional coking operation. Following the completion or substantial completion of the coking operation, the test container is recovered and from the conventional converted coke and the sample(s) of coke are removed from the container for testing and evaluation. The container is recharged with one or more additional samples of coke and reused in another conventional coking operation.

25 Claims, 15 Drawing Sheets

(56) References Cited

U.S. PATENT DOCUMENTS

| | | | |
|---|---|---|---|
| 1,818,370 A | 8/1931 | Wine | |
| 1,848,818 A | 3/1932 | Becker | |
| 1,955,962 A * | 4/1934 | Jones | 434/367 |
| 2,394,173 A | 2/1946 | Harris et al. | |
| 2,424,012 A | 7/1947 | Bangham et al. | |
| 2,902,991 A | 9/1959 | Whitman | |
| 3,462,345 A | 8/1969 | Kernan | |
| 3,545,470 A | 12/1970 | Paton | |
| 3,616,408 A | 10/1971 | Hickam | |
| 3,630,852 A | 12/1971 | Nashan et al. | |
| 3,652,403 A | 3/1972 | Knappstein et al. | |
| 3,676,305 A | 7/1972 | Cremer | |
| 3,709,794 A | 1/1973 | Kinzler et al. | |
| 3,746,626 A | 7/1973 | Morrison, Jr. | |
| 3,748,235 A | 7/1973 | Pries | |
| 3,784,034 A | 1/1974 | Thompson | |
| 3,806,032 A | 4/1974 | Pries | |
| 3,836,161 A | 9/1974 | Buhl | |
| 3,839,156 A | 10/1974 | Jakobi et al. | |
| 3,844,900 A | 10/1974 | Schulte | |
| 3,857,758 A | 12/1974 | Mole | |
| 3,875,016 A | 4/1975 | Schmidt-Balve et al. | |
| 3,876,506 A | 4/1975 | Dix et al. | |
| 3,878,053 A | 4/1975 | Hyde | |
| 3,897,312 A | 7/1975 | Armour et al. | |
| 3,906,992 A | 9/1975 | Leach | |
| 3,912,091 A | 10/1975 | Thompson | |
| 3,917,458 A | 11/1975 | Polak | |
| 3,930,961 A | 1/1976 | Sustarsic et al. | |
| 3,957,591 A | 5/1976 | Riecker | |
| 3,959,084 A | 5/1976 | Price | |
| 3,963,582 A | 6/1976 | Helm et al. | |
| 3,984,289 A | 10/1976 | Sustarsic et al. | |
| 4,004,702 A | 1/1977 | Szendroi | |
| 4,004,983 A | 1/1977 | Pries | |
| 4,040,910 A | 8/1977 | Knappstein et al. | |
| 4,059,885 A | 11/1977 | Oldengott | |
| 4,067,462 A | 1/1978 | Thompson | |
| 4,083,753 A | 4/1978 | Rogers et al. | |
| 4,086,231 A | 4/1978 | Ikio | |
| 4,100,033 A | 7/1978 | Holter | |
| 4,111,757 A | 9/1978 | Ciarimboli | |
| 4,124,450 A | 11/1978 | MacDonald | |
| 4,141,796 A | 2/1979 | Clark et al. | |
| 4,145,195 A | 3/1979 | Knappstein et al. | |
| 4,147,230 A | 4/1979 | Ormond et al. | |
| 4,189,272 A | 2/1980 | Gregor et al. | |
| 4,194,951 A | 3/1980 | Pries | |
| 4,196,053 A | 4/1980 | Grohmann | |
| 4,211,608 A | 7/1980 | Kwasnoski et al. | |
| 4,213,489 A | 7/1980 | Cain | |
| 4,213,828 A | 7/1980 | Calderon | |
| 4,222,748 A | 9/1980 | Argo et al. | |
| 4,225,393 A | 9/1980 | Gregor et al. | |
| 4,235,830 A | 11/1980 | Bennett et al. | |
| 4,248,671 A | 2/1981 | Belding | |
| 4,249,997 A | 2/1981 | Schmitz | |
| 4,263,099 A | 4/1981 | Porter | |
| 4,285,772 A | 8/1981 | Kress | |
| 4,287,024 A | 9/1981 | Thompson | |
| 4,289,584 A | 9/1981 | Chuss et al. | |
| 4,289,585 A | 9/1981 | Wagener et al. | |
| 4,303,615 A * | 12/1981 | Jarmell et al. | 422/557 |
| 4,307,673 A | 12/1981 | Caughey | |
| 4,314,787 A | 2/1982 | Kwasnik et al. | |
| 4,330,372 A | 5/1982 | Cairns et al. | |
| 4,334,963 A | 6/1982 | Stog | |
| 4,336,843 A | 6/1982 | Petty | |
| 4,340,445 A | 7/1982 | Kucher et al. | |
| 4,342,195 A | 8/1982 | Lo | |
| 4,344,820 A | 8/1982 | Thompson | |
| 4,366,029 A | 12/1982 | Bixby et al. | |
| 4,373,244 A | 2/1983 | Mertens et al. | |
| 4,375,388 A | 3/1983 | Hara et al. | |
| 4,392,824 A | 7/1983 | Struck et al. | |
| 4,395,269 A | 7/1983 | Schuler | |
| 4,396,394 A | 8/1983 | Li et al. | |
| 4,396,461 A | 8/1983 | Neubaum et al. | |
| 4,431,484 A | 2/1984 | Weber et al. | |
| 4,439,277 A | 3/1984 | Dix | |
| 4,445,977 A | 5/1984 | Husher | |
| 4,446,018 A | 5/1984 | Cerwick | |
| 4,448,541 A | 5/1984 | Wirtschafter | |
| 4,452,749 A | 6/1984 | Kolvek et al. | |
| 4,459,103 A * | 7/1984 | Gieskieng | 432/43 |
| 4,469,446 A | 9/1984 | Goodboy | |
| 4,508,539 A | 4/1985 | Nakai | |
| 4,527,488 A | 7/1985 | Lindgren | |
| 4,568,426 A * | 2/1986 | Orlando | 203/1 |
| 4,570,670 A | 2/1986 | Johnson | |
| 4,614,567 A | 9/1986 | Stahlherm et al. | |
| 4,645,513 A | 2/1987 | Kubota et al. | |
| 4,655,193 A | 4/1987 | Blacket | |
| 4,655,804 A | 4/1987 | Kercheval et al. | |
| 4,680,167 A * | 7/1987 | Orlando | 422/199 |
| 4,704,195 A | 11/1987 | Janicka et al. | |
| 4,720,262 A | 1/1988 | Durr et al. | |
| 4,726,465 A | 2/1988 | Kwasnik et al. | |
| 4,929,179 A | 5/1990 | Breidenbach et al. | |
| 4,941,824 A | 7/1990 | Holter et al. | |
| 5,052,922 A | 10/1991 | Stokman et al. | |
| 5,062,925 A | 11/1991 | Durselen et al. | |
| 5,078,822 A | 1/1992 | Hodges et al. | |
| 5,114,542 A | 5/1992 | Childress et al. | |
| 5,227,106 A | 7/1993 | Kolvek | |
| 5,228,955 A | 7/1993 | Westbrook, III | |
| 5,318,671 A | 6/1994 | Pruitt | |
| 5,670,025 A | 9/1997 | Baird | |
| 5,928,476 A | 7/1999 | Daniels | |
| 5,968,320 A | 10/1999 | Sprague | |
| 6,017,214 A | 1/2000 | Sturgulewski | |
| 6,059,932 A | 5/2000 | Sturgulewski | |
| 6,139,692 A | 10/2000 | Tamura et al. | |
| 6,152,668 A | 11/2000 | Knoch | |
| 6,187,148 B1 | 2/2001 | Sturgulewski | |
| 6,189,819 B1 | 2/2001 | Racine | |
| 6,290,494 B1 | 9/2001 | Barkdoll | |
| 6,596,128 B2 | 7/2003 | Westbrook | |
| 6,626,984 B1 | 9/2003 | Taylor | |
| 6,699,035 B2 | 3/2004 | Brooker | |
| 6,758,875 B2 | 7/2004 | Reid et al. | |
| 6,907,895 B2 | 6/2005 | Johnson et al. | |
| 6,946,011 B2 | 9/2005 | Snyder | |
| 7,056,390 B2 | 6/2006 | Fratello et al. | |
| 7,077,892 B2 | 7/2006 | Lee | |
| 7,314,060 B2 | 1/2008 | Chen et al. | |
| 7,331,298 B2 | 2/2008 | Barkdoll et al. | |
| 7,497,930 B2 | 3/2009 | Barkdoll et al. | |
| 7,611,609 B1 | 11/2009 | Valia et al. | |
| 7,644,711 B2 | 1/2010 | Creel | |
| 7,727,307 B2 | 6/2010 | Winkler | |
| 7,803,627 B2 | 9/2010 | Hodges | |
| 7,827,689 B2 | 11/2010 | Crane et al. | |
| 7,998,316 B2 | 8/2011 | Barkdoll | |
| 8,071,060 B2 | 12/2011 | Ukai et al. | |
| 8,079,751 B2 | 12/2011 | Kapila et al. | |
| 8,236,142 B2 | 8/2012 | Westbrook | |
| 8,266,853 B2 | 9/2012 | Bloom et al. | |
| 8,398,935 B2 | 3/2013 | Howell, Jr. et al. | |
| 2006/0102420 A1 | 5/2006 | Huber et al. | |
| 2007/0205091 A1 | 9/2007 | Barkdoll et al. | |
| 2008/0169578 A1 | 7/2008 | Crane et al. | |
| 2008/0179165 A1 | 7/2008 | Chen et al. | |
| 2008/0271985 A1 | 11/2008 | Yamasaki | |
| 2009/0217576 A1 | 9/2009 | Kim et al. | |
| 2009/0283395 A1 | 11/2009 | Hippe | |
| 2010/0095521 A1 | 4/2010 | Bertini et al. | |
| 2010/0115912 A1 | 5/2010 | Worley | |
| 2010/0236914 A1 | 9/2010 | Bardkoll | |
| 2010/0287871 A1 | 11/2010 | Bloom et al. | |
| 2011/0223088 A1 | 9/2011 | Chang et al. | |
| 2011/0253521 A1 | 10/2011 | Kim | |
| 2012/0024688 A1 | 2/2012 | Barkdoll | |
| 2012/0030998 A1 | 2/2012 | Barkdoll et al. | |

(56) References Cited

U.S. PATENT DOCUMENTS

| | | |
|---|---|---|
| 2012/0152720 A1 | 6/2012 | Reichelt et al. |
| 2012/0228115 A1 | 9/2012 | Westbrook |
| 2013/0216717 A1 | 8/2013 | Rago et al. |
| 2014/0033917 A1 | 2/2014 | Rodgers et al. |
| 2014/0048402 A1 | 2/2014 | Quanci et al. |
| 2014/0048404 A1 | 2/2014 | Quanci et al. |
| 2014/0048405 A1 | 2/2014 | Quanci et al. |
| 2014/0083836 A1 | 3/2014 | Quanci et al. |
| 2014/0182195 A1 | 7/2014 | Quanci et al. |
| 2014/0182683 A1 | 7/2014 | Quanci et al. |
| 2014/0183023 A1 | 7/2014 | Quanci et al. |
| 2014/0183024 A1 | 7/2014 | Chun et al. |
| 2014/0183026 A1 | 7/2014 | Quanci et al. |
| 2014/0262139 A1 | 9/2014 | Choi et al. |
| 2014/0262726 A1 | 9/2014 | West et al. |

FOREIGN PATENT DOCUMENTS

| | | |
|---|---|---|
| CN | 1092457 | 9/1994 |
| CN | 1255528 | 6/2000 |
| CN | 2528771 | 2/2002 |
| CN | 1358822 | 7/2002 |
| CN | 1468364 | 1/2004 |
| CN | 2668641 Y | 1/2005 |
| CN | 2509188 | 11/2011 |
| CN | 202226816 | 5/2012 |
| DE | 212176 C | 7/1909 |
| DE | 3329367 C | 2/1921 |
| DE | 19545736 A1 | 6/1997 |
| DE | 19803455 C1 | 8/1999 |
| DE | 10154785 A1 | 5/2003 |
| FR | 2339664 A1 | 8/1977 |
| GB | 441784 A | 1/1936 |
| GB | 606340 A | 8/1948 |
| GB | 611524 A | 11/1948 |
| GB | 725865 A | 3/1955 |
| JP | 54054101 A | 4/1979 |
| JP | 57051786 A | 3/1982 |
| JP | 57051787 A | 3/1982 |
| JP | 57083585 A | 5/1982 |
| JP | 57090092 A | 6/1982 |
| JP | 58091788 A | 5/1983 |
| JP | 59051978 A | 3/1984 |
| JP | 59053589 A | 3/1984 |
| JP | 59071388 A | 4/1984 |
| JP | 59108083 A | 6/1984 |
| JP | 59145281 A | 8/1984 |
| JP | 60004588 A | 1/1985 |
| JP | 61106690 A | 5/1986 |
| JP | 62011794 A | 1/1987 |
| JP | 62285980 | 12/1987 |
| JP | 01103694 A | 4/1989 |
| JP | 01249886 A | 10/1989 |
| JP | H0319127 | 3/1991 |
| JP | 07188668 | 7/1995 |
| JP | 07216357 | 8/1995 |
| JP | 08127778 A | 5/1996 |
| JP | 2001200258 A | 7/2001 |
| JP | 03197588 B2 | 8/2001 |
| JP | 2002106941 A | 4/2002 |
| JP | 2003041258 A | 2/2003 |
| JP | 2003071313 A | 3/2003 |
| JP | 04159392 B2 | 10/2008 |
| JP | 2009144121 A | 7/2009 |
| JP | 2012102302 A | 5/2012 |
| KR | 1019960008754 | 10/1996 |
| KR | 1019990054426 | 7/1999 |
| KR | 10-0797852 | 1/2008 |
| KR | 1020110010452 | 2/2011 |
| KR | 10-0296700 B1 | 10/2011 |
| KR | 101318388 B1 | 10/2013 |
| WO | WO-9012074 A1 | 10/1990 |
| WO | WO-9945083 A1 | 9/1999 |
| WO | WO-2007103649 A2 | 9/2007 |
| WO | WO 2008/034424 | 3/2008 |
| WO | WO-2010107513 A1 | 9/2010 |
| WO | WO 2012/029979 | 3/2012 |

OTHER PUBLICATIONS

Crelling et al., "Effects of Weathered Coal on Coking Properties and Coke Quality", Fuel, 1979, vol. 58, Issue 7, pp. 542-546.

Diez, et al., "Coal for Metallurgical Coke Production: Predictions of Coke Quality and Future Requirements for Cokemaking", International Journal of Col Geology, 2002, vol. 50, Issue 1-4, pp. 389-412.

International Search Report and Written Opinion for PCT/US2013/054737 mailed on Nov. 18, 2013, 10 pages.

Rose, Harold J., "The Selection of Coals for the Manufacture of Coke", American Institute of Mining and Metallurgical Engineers, Feb. 1926, 8 pages.

Clean coke process: process development studies by USS Engineers and Consultants, Inc., Wisconsin Tech Search, request date Oct. 5, 2011, 17 pages.

Database WPI, Week 199115, Thomson Scientific, Lond, GB; AN 1991-107552.

JP 03-197588, Inoqu Keizo et al., Method and Equipment for Boring Degassing Hole in Coal Charge in Coke Oven, Japanese Patent (Abstract Only) Aug. 28, 1991.

JP 04-159392, Inoue Keizo et al., Method and Equipment for Opening Hole for Degassing of Coal Charge in Coke Oven, Japanese Patent (Abstract Only) Jun. 2, 1992.

* cited by examiner ial applications and coke is typically pro-
METHOD AND APPARATUS FOR TESTING COAL COKING PROPERTIES

BACKGROUND OF THE INVENTION

The present innovations relate generally to the field of producing coke from coal and more particularly to a method and apparatus for testing and evaluating the coking quality of coal in a commercial coke oven.

Coke is a key ingredient used in the manufacture of steel and other commercduced by heating coal in a controlled atmosphere for long periods of time to drive off volatile materials and impurities from coal and convert or reduce the coal to coke. Because coal is an organic material the components of coal can vary widely and this wide variation in components results in disparate coking capabilities for coal mined from different locations. Some coal can be converted into high quality, metallurgical coke and some lack the necessary components or have too many impurities and result in a poor quality coke. Due to the wide range of coking qualities of coke, it is necessary to test the coking performance of coal and test the coking performance of various blends of coal. Unfortunately, there is an inadequate supply of testing ovens for evaluating the coking performance of coal and blends of coal and therefore, there is a need for developing some means for testing the coking performance of coal and blends of coal as part of continuously operating commercial coke oven operation. In the past, expendable, single-use containers have been used during a commercial coke oven operation in order to test the coking performance of coal samples. However, the expendable, single-use containers such as cardboard have been consumed in the extreme environment of the commercial coke oven and once the container has been consumed, or otherwise destroyed, it can be difficult to recover the sample of coal which has been at least partially converted into coke and the consumed material may leave behind ash or undesirable impurities in the converted coke.

SUMMARY OF THE INVENTION

The innovations include a method of evaluating the coking properties of coal produced in a coking oven comprising providing a certain quantity of coal to be tested and a test container intended to receive the quantity of test coal. The test container can have varying degrees of gas permeability to allow the gases and other volatiles emitted from the coal to be escape the container. The container is positioned in a coking oven along with a charge of coking coal. Ideally, the container is substantially surrounded by the coking coal, at least on the sides of the container and potentially also on the top and bottom of the container. The test coal, test container and supply of coking coal are heated in the coking oven to reduce or convert at least a portion of the test coal to coke and then the container along with the remaining supply of coking coal and coke converted therefrom are removed from the coking oven. The test container is recovered for re-use and the quantity of test coal and coke converted therefrom are recovered and removed from the test container for evaluation.

The test container is reused by positioning a second quantity of test coal in the test container and positioning the test container in a coking oven along with a charge of a second supply of coking coal. The second quantity of test coal, the testing container, and the second supply of coking coal are heated in the oven to reduce at least a portion of coal into coke. The test container and the material contained therein are removed from the oven and the second quantity of test coal is removed from the test container for evaluation. The test container can once again be repaired, if necessary, and re-used for yet another test.

The method can be modified to use a container which includes a barrier liner and/or a test container which includes thermally insulating material positioned between at least a portion of the test container and the quantity of test coal. In another modification, the supply of coking coal can be formed into a substantially solid charge before the coking operation and the test container can be positioned into a recess formed in the substantially solid charge.

Another innovation relates to the structure of a container used for evaluating the coking properties of coal in a horizontal heat recovery coking oven. This container is formed from a bottom member, a top member and at least one side member extending between the top and bottom members. The various members of the test container hold a test sample of coal which is intended to be reduced, at least in part, to coke in a coking oven. The container is designed so that it will not be consumed or destroyed during the high heat and harsh reducing environment of the coking oven and is also designed to be gas permeable so that the gases and other volatile compounds in the coal can escape during the coking operation. One of the various members of the test container is selectively moveable relative to the others so that the container can be opened and loaded with a supply of test coal and then closed to more fully contain the test coal inside the container. The various member of the container can be formed from a variety of materials including steel, ceramics, and refractory insulating materials. Various features can be integrated into the container to facilitate easy of movement of the container by machinery such as one or more loading lugs adapted for use with a crane or one or more channels adapted to receive the forks of a fork lift. While the structure of the container lends itself for use in a horizontal heat recovery coking oven, it is understood that the container can be used in any coking oven.

DETAILED DESCRIPTION OF THE PREFERRED EMBODIMENTS

Figure 1:
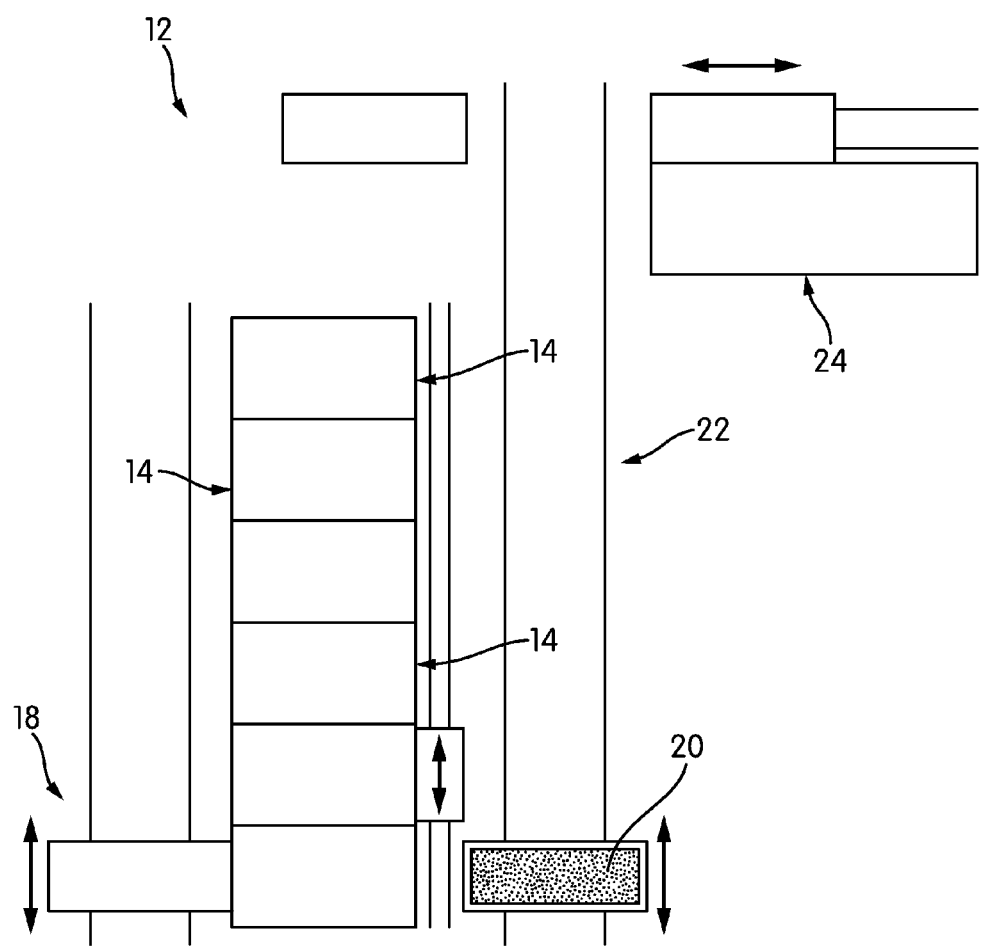
FIG. 1 is an overhead schematic view of a portion of a bank of horizontal heat recovery coking ovens.

Referring to FIG. 1, a schematic view of a portion of a commercial coke oven operation 12 is shown. Ideally, the coke ovens used are horizontal heat recovery coke ovens, but the processes and articles described herein are suitable for use with any coke ovens. The coke oven operation 12 comprises a bank of individual coke ovens 14 adapted to receive a supply of coking coal 16 (FIG. 6) from a conveyor and loading ram system 18. The conveyor and loading ram 18 insert a charge of coking coal 16 into the coke oven 14 in which the coking coal 16 is subject to high heat for an extended period of time which drives off the volatile materials and gases in the coking coal 16 resulting in the conversion of the coking coal 16 into coke 20. After the conversion process, the coke 20 is removed from the oven 14 and transported via a conveyor 22 to a quenching and sizing facility 24 where the hot coke 20 is cooled and broken up into pieces of coke of a desired size.

The coke oven operation 12 typically includes dozens and dozens of individual coke ovens 14 processing tons of coal each day to generate coke for use in commercial operations such as steelmaking. The coke oven operation 12 typically runs continuously, immediately loading a new charge of coking coal 16 as soon as the coke oven 14 has been cleared following a coking cycle. Continuous operation of the ovens 14 allows the efficiency of using the latent heat in the coke oven 14 from one coking operation in the next cycle. Because of the relative size of the coke ovens 14, the large capital investment in such structures and the high heat required for each coking cycle, it is critically important that each coke oven 14 be run substantially continuously with minimal downtime.

Coal, the raw material used to create coke, is an organic material which can vary greatly in its properties from coal mine to coal mine. In view of these variabilities inherent in the raw material and the significant capital investment in the coke oven operations, an operator must have some means for effectively and efficiently testing the coking performance of particular coals or coal blends before committing an entire coke oven 14 or battery of ovens to converting the coal. As seen in FIGS. 2-6, a test container 30 is provided which can be used during a conventional, commercial coking operation to allow an operator to use a coke oven 14 to convert a conventional charge of coking coal 16 while simultaneously converting a quantity of test coal. The test container 30 comprises a bottom member 32 or bottom wall, a side member or plurality of side walls 34 provided thereon and a top member 36 or top wall. As seen in FIGS. 2-6, the test container is rectangular in shape with four side walls 34 extending between the bottom and top members, 32 and 36 respectively, however, any number of side members could be used, for example, a single, cylindrical shaped side member could be used, or any other number of configurations depending upon the particular needs of the situation. Ideally, the structural elements of the test container are formed of steel or some other material which is adapted to survive the harsh environment inside the coke oven 14. For example, the top member 36 and side walls 34 can be formed from ⅜ths inch steel and the bottom wall can be formed from ½ inch steel. The bottom member 32 is preferably mounted to the side walls 34 by the flanges 38 welded to the bottom member 32 which are in turn attached via bolts 40 to suitable apertures in the side wall 34. Similarly, the side walls 34 are attached to one another by cooperating flanges 42 emanating from the side walls 34 which are attached to one another by bolts 40. The top member 36 is removably mounted to the side walls 34 by bolts 40 extending through suitable apertures in the top member 36 and a flange provided at the uppermost end of the side walls 34.

In order to provide for ease of transportation and movement of the test container 30, a plurality of lugs 46 can be provided on the side walls 34 or other suitable locations so that the container can be lifted by a crane or other piece of machinery. Although lugs 46 are shown, it is understood that a variety of different structures can be integrated into the test container 30 to allow securing the test container for movement such as pad-eyes, points, hooks, apertures, or the like. Channels 48 may also be mounted to the side walls 34 and/or bottom member 32 and the channels 48 can be sized to receive the forks of a conventional forklift to permit easy transportation of the test container 30. Still another design element of the test container 30 are one or more gussets 50 attached to the side walls 34 to give added strength and rigidity to the container 30 for enduring the tortuous coking operation. Similarly, skis 54 or other abrasion resistant members can be welded to the bottom member 32 to assist in the sliding movement of the test container. For example, when the test container 30 is loaded into the coke oven 14, it will likely be necessary to slide the container 30 along the bottom wall of the oven and the skis 54 can assist in this sliding action.

Figure 2:
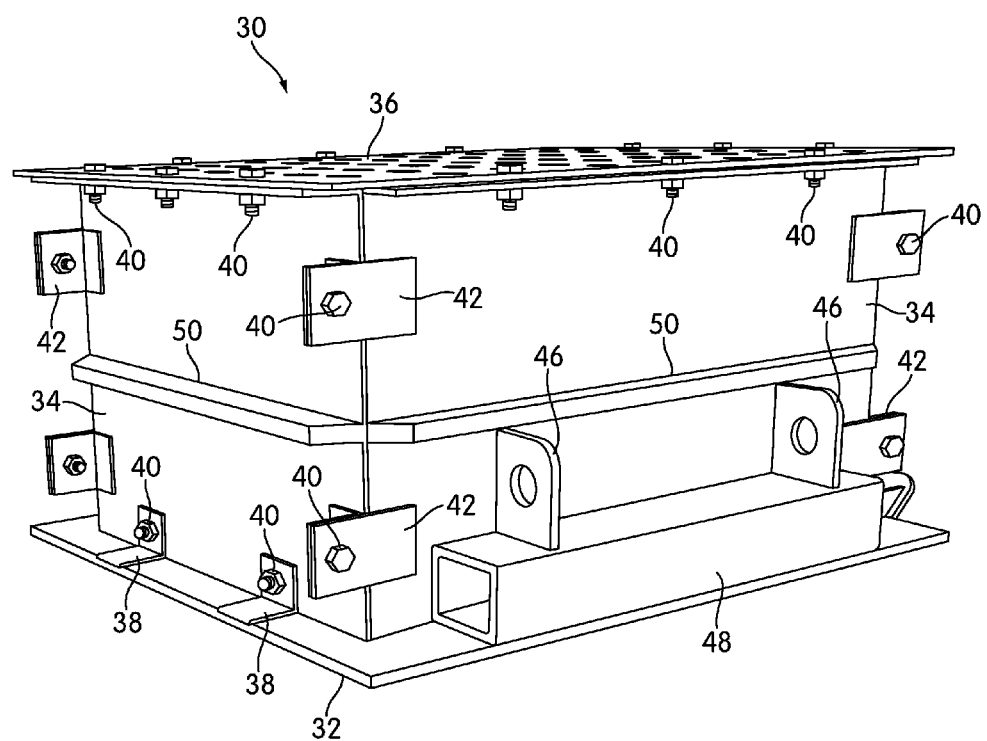
FIG. 2 is a perspective view of reusable test container.
Figure 3:
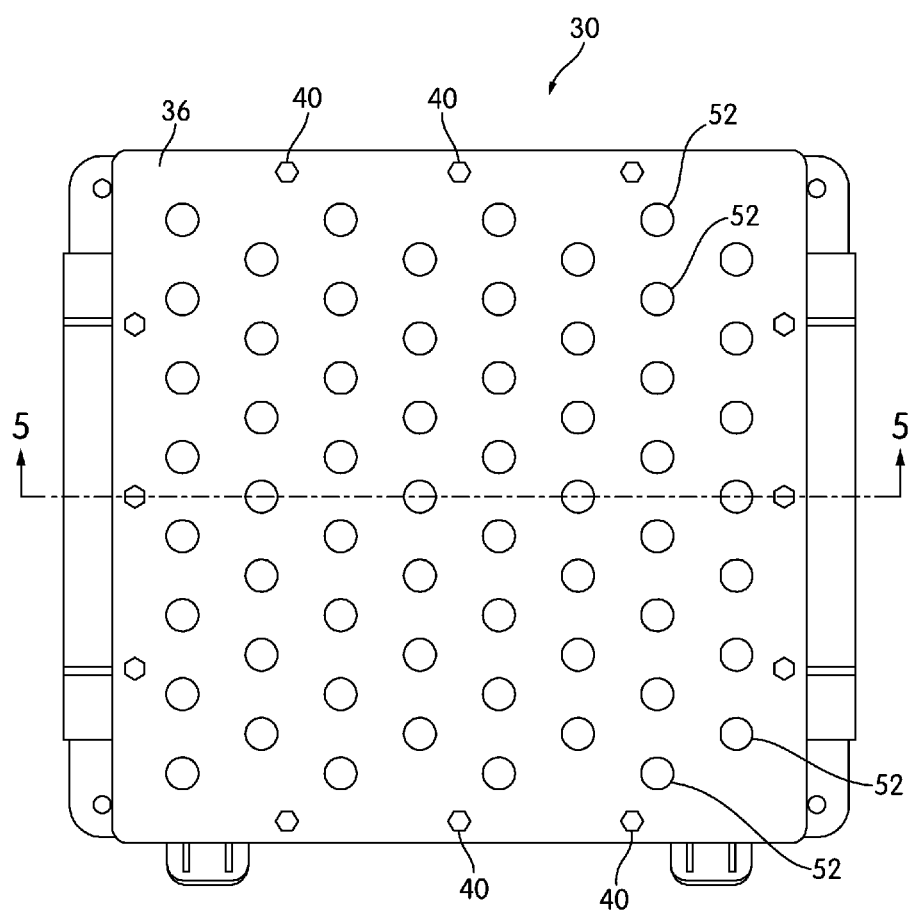
FIG. 3 is a top view of the reusable test container seen in FIG. 2.
Figure 4:
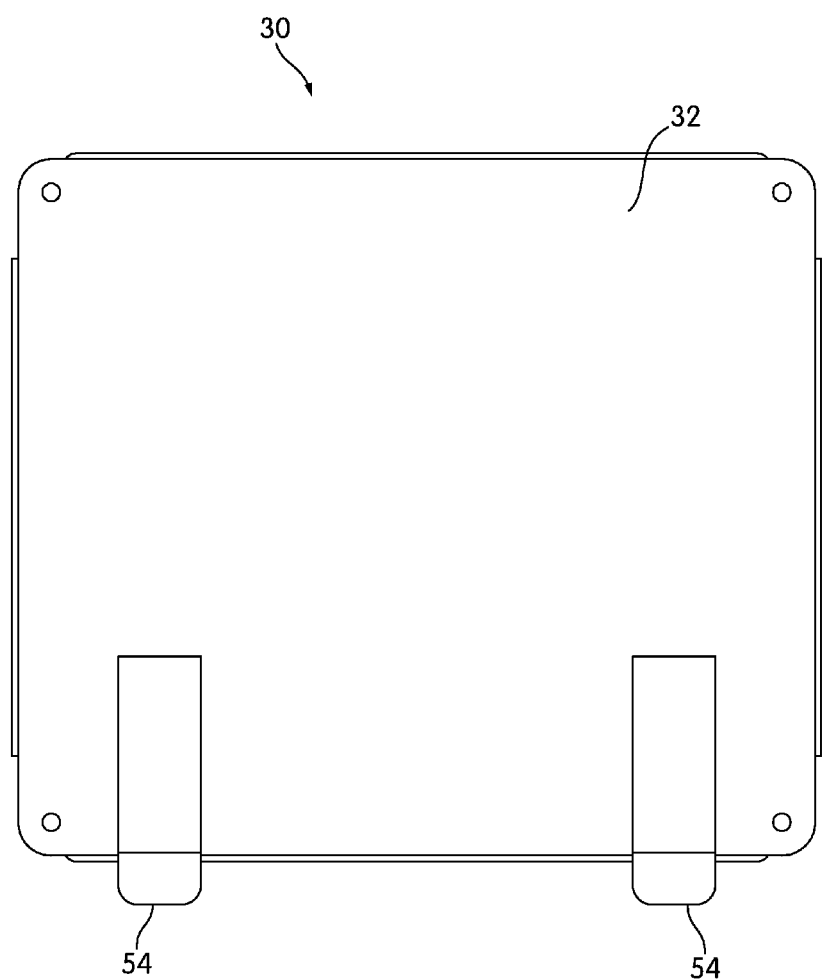
FIG. 4 is a bottom view of the reusable test container seen in FIG. 2.
Figure 5:
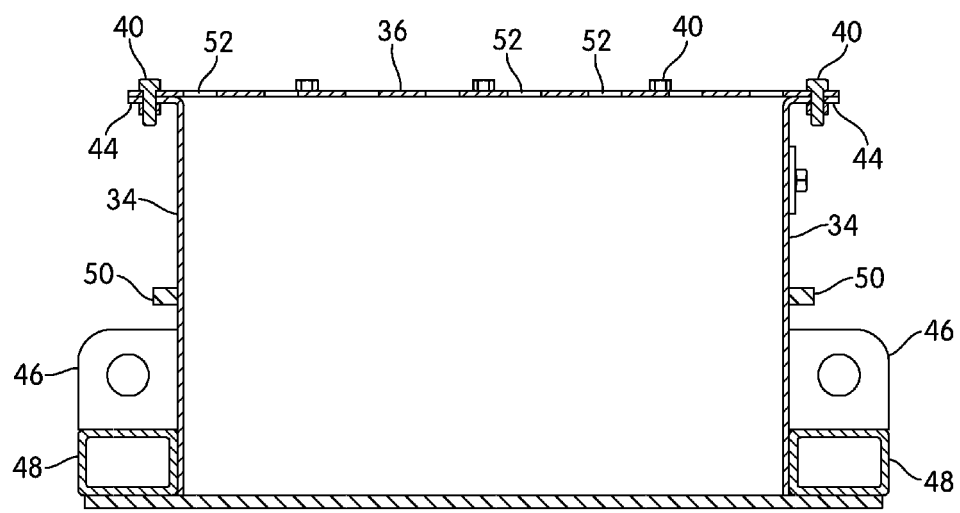
FIG. 5 is a sectional view of the reusable test container taken along lines 5-5 of FIG. 3.

During the coking operation, the high heat inside the coke oven 14 drives off from the test coal impurities and other volatile materials in the form of gases and therefore, the container should provide some means for the gaseous material to escape. As seen in FIGS. 2 and 3, the test container 30 incorporates multiple apertures 52 formed on the top member 36 to allow these gaseous materials to escape the container 30. These apertures 52 can also be valuable for allowing quenching fluid to enter and exit the test container 30 during the conventional quenching of the coke produced. Some of the quenching fluid would be expected to be converted to gas form during the quenching operation and therefore, the apertures 52 also permit the escape of this gas during the conventional quenching step of the process. Although not seen in the FIGS. 2-6, one or more apertures may also be formed on the bottom wall 32 to allow the flow of gases, quenching fluid or quenching steam to escape from the test container 30.

Figure 6:
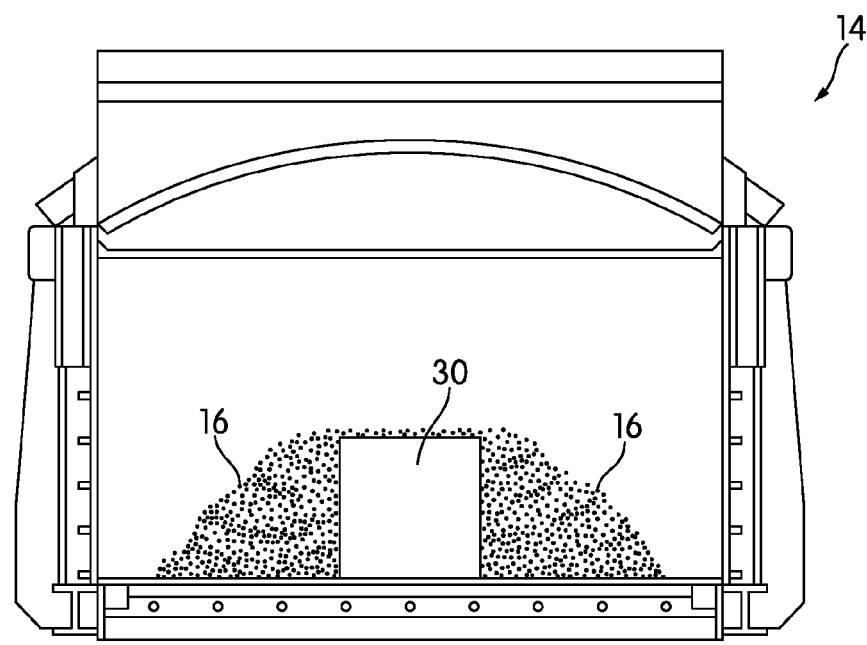
FIG. 6 is a view of a portion of a horizontal heat recovery coking oven having the test container and the supply of coking coal contained therein.
Figure 7:
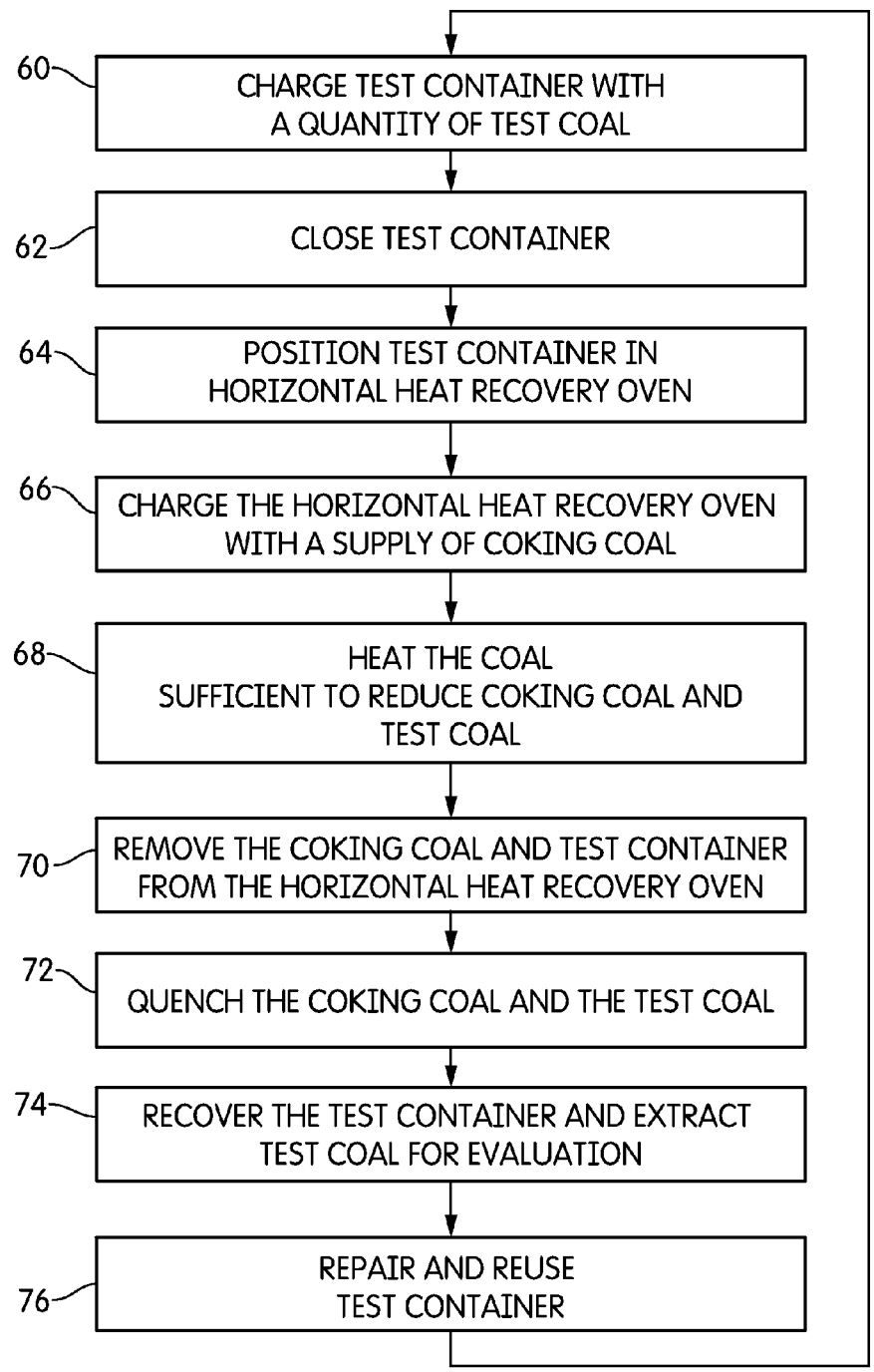
FIG. 7 is a schematic flow chart of a method for evaluating the coking properties of coal in a coking oven using a reusable test container as described herein.

FIG. 7 provides a schematic flow chart of a method of using the test container during a conventional coke oven operation. A key benefit of this method is that it allows for testing of a coal sample as part of the continued commercial operation of the coke oven operations. Using this process and equipment, the commercial coke oven cycle time and operation can be maintained with substantially the same coke production. The method begins with a charge of test coal being loaded 60 and in some cases packed into the test container 30 and then the test container is closed 62. The test container is loaded into the coking oven 64 along with a supply of coking coal 66. As seen in FIG. 6, the test container 62 is ideally centrally located within the coking oven 14 both from side to side and front to back. Ideally the supply of coking coal 16 is packed around the test container to substantially surround all the side walls 34 and in some instances, the top member 36 of the container 30. Both the supply of coking coal 16 and the test coal inside the test container 30 are subjected to heat from the coke oven 14 in a closely controlled atmosphere for a sufficient period of time to drive off the impurities and volatile matter converting at least a portion of the coal to coke. Once this conversion process is complete, the conventional converted coke, the test container and the test coal (now coke) contained therein, are removed from the coking oven 70. The converted coke and converted test coal are quenched 72 and then the test container 30 and converted test coal are recovered from the quenched material for evaluation and analysis of the coking capabilities of the test coal 74. The converted test coal is removed from the container by removing the bolts 40 holding the top 36 to the sidewalls 34 of the test container. Alternatively, the bolts can be removed so that one of the side walls 34 of the test container is removed. Still another means of removing the converted test coal would be to remove enough bolts 40 so the top 36 and at least one sidewall 34 are removed or two side walls 34 are removed from the balance of the test container 30. The test container 30 is then repaired, if necessary, and then reused 76 for a second testing operation of second quantity of test coal as described above. Please note, the conversion process described above suggests that a complete conversion of coal to coke is accomplished for both the supply of coking coal and test coal, but it is to be understood that complete conversion is not necessarily achieved and therefore, conversion as described herein is understood to mean both complete or partial conversion of coal to coke.

By following the process outlined above, the coking oven receives substantially a full charge of conventional coking coal and therefore, the coking cycle of the oven continues to operate at substantially full commercial capacity while still allowing for the testing of the coking quality of coal blends and coal samples in a commercial environment. In order to evaluate any adverse effects of coking two different coal blends during the same coking cycle (one coal blend inside the test container 30 and a second, different coal blend loaded into the coking oven around the container) testing has shown no different coking performance resulting from this process. First, coal blend A was converted inside a test container with a different coal blend B in the coking oven and second, coal blend A was converted in the same oven under the same operating conditions and no appreciable coking properties were realized between coal blend A used in the test container as compared to coal blend A which was coked by the conventional process.

One key benefit of the test container as described herein is the fact that the container is designed and intended to be reused in at least two coal to coke conversions. Through the use of suitable materials such as the steel and ceramic materials described above along with the specific design, the container can be used for multiple coking cycles with little or no repair. This ability to reuse the test container reduces costs and waste from the testing operation.

Figure 8:
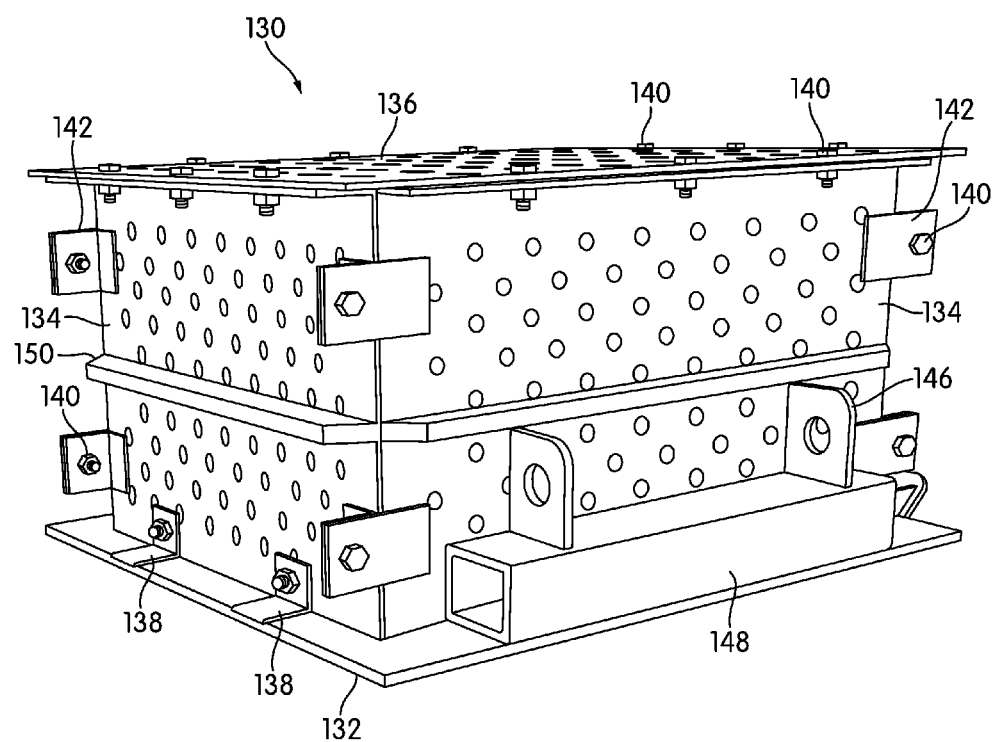
FIG. 8 is a perspective view of a second reusable test container suitable for use in evaluating the coking properties of coal in a coking oven.
Figure 9:
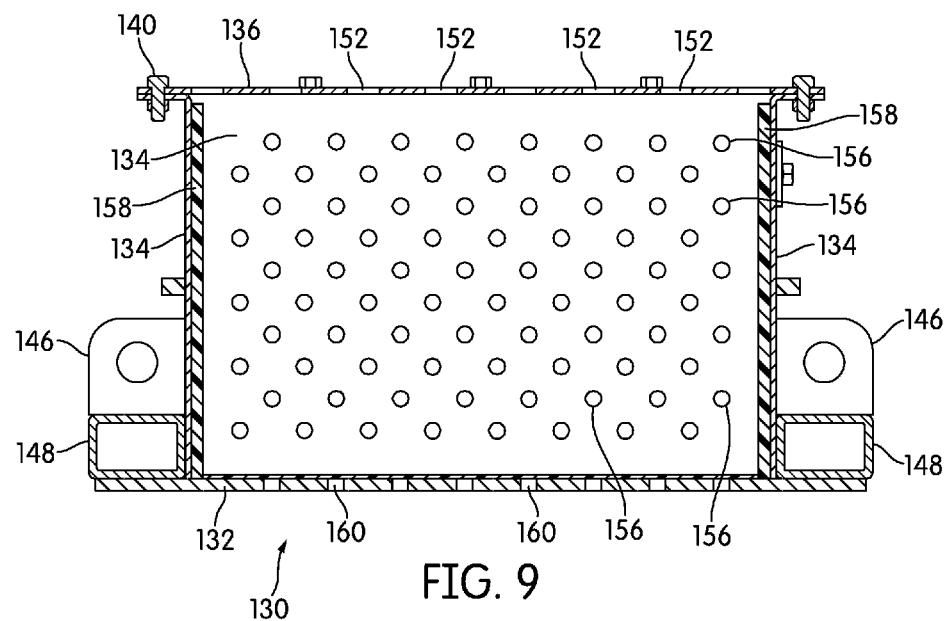
FIG. 9 is a sectional view of the second reusable test container of FIG. 8 similar to the view of the first reusable test container as seen in FIG. 3.

The structure of the test container can be altered in various ways to alter the performance of the container during the coking operation. FIGS. 8 and 9 show another embodiment of a test container similar to that seen in FIGS. 2-5. In describing this other embodiment, the same reference numerals will be used, but increased by 100 as the embodiment depicted in FIGS. 2-5. In this embodiment, the test container 130 has the same general shape with side walls 134 secured to a bottom member 132 with a top member 136 selectively mounted to the side walls 134. However, in this embodiment, apertures 152 are formed in the top member 136 along with multiple apertures 156 formed in the side walls 134 to permit the free flow of gaseous volatile material from the test coal during the coking operation. In one embodiment, the apertures 156 are 0.75 inches in cross section, but the size of the apertures can range from $\frac{1}{8}^{th}$ to 2 inches in cross section. Persons skilled in the art can alter the size, number, shape and location of the apertures to best suit the coking operations. For example, circular apertures are shown herein, but a wide variety of aperture shapes or configurations can be used including oval slots, squares, rectangular openings, etc. The apertures can be formed in only the top member 136, one or more side walls 134, only the bottom member 132 or any combination of these various elements.

When steel or some other metal is used to construct the test container, there can be undesirable heat transfer from the structural members of the container to the test coal. One solution to this is to provide thermally insulating materials intermediate the some or all of the members of the test container and the test coal. As seen in FIG. 9, layers of thermally insulating material 158 have been provided on the inside of the container intermediate the side walls 134 and the test coal. With this structure, adverse effects resulting from conduction of heat from the side walls 134 to the test coal can be minimized or eliminated. FIG. 9 depicts insulating materials only adjacent the side walls 134. It is to be understood that insulating materials can be used adjacent the top member 136, one or more side walls 134, only the bottom member 132 or any combination of these various elements. FIG. 9 also depicts the use of a barrier material 160 positioned on top of the bottom member 132. When apertures 160 are provided in the bottom member 132, it can be beneficial to insert a barrier material 160 between the test charge and the bottom member 132 to prevent small pieces of the test charge from passing through the apertures 160 and potentially contaminating the conventional coal charge surrounding the test container 130. A thin layer of plastic resin material can be used and, depending upon the resin material used, this product can be fully consumed during the coking operation leaving no residue or impurities behind.

Figure 10:
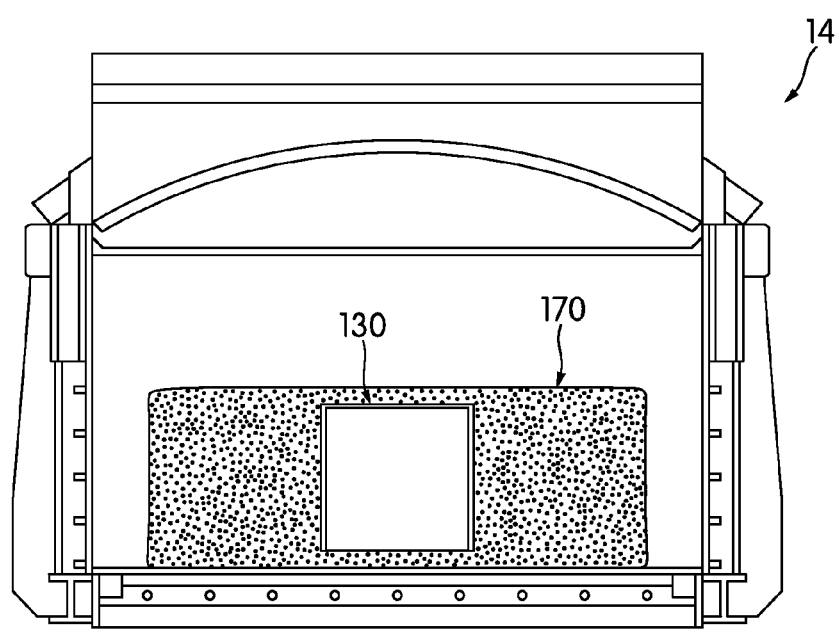
FIG. 10 is a view of a portion of a horizontal heat recovery coking oven having the test container provided in a stamped charge supply of coking coal.

The coking process depicted in FIG. 6 shows the test container loosely surrounded by a charge of coal to be coked. One alternative to this process is to create a stamped charge or brick of coal to be coked. As seen in FIG. 10, the conventional coal to be coked is first formed into a stamped charge 170 resembling a large brick before it is loaded into the coke oven 14. Using the test container 130 according to this variation on the process is largely the same as schematically described in FIG. 7, however, before loading the stamped charge 170 into the coking oven, a recess or hollowed out section must be formed in the stamped charge 170. The test container 130 is placed inside this recess or hollowed out section and it is preferred that the shape and contour of the recess be as close as practical to the contours of the test container 130 to minimize the open air space around the test container 130. One option is to place loose coal in the space between the exterior surfaces of the test container 130 and the surface of the recess after the test container is positioned in the charge 170 to avoid air pockets inside the charge 170.

Figure 14:
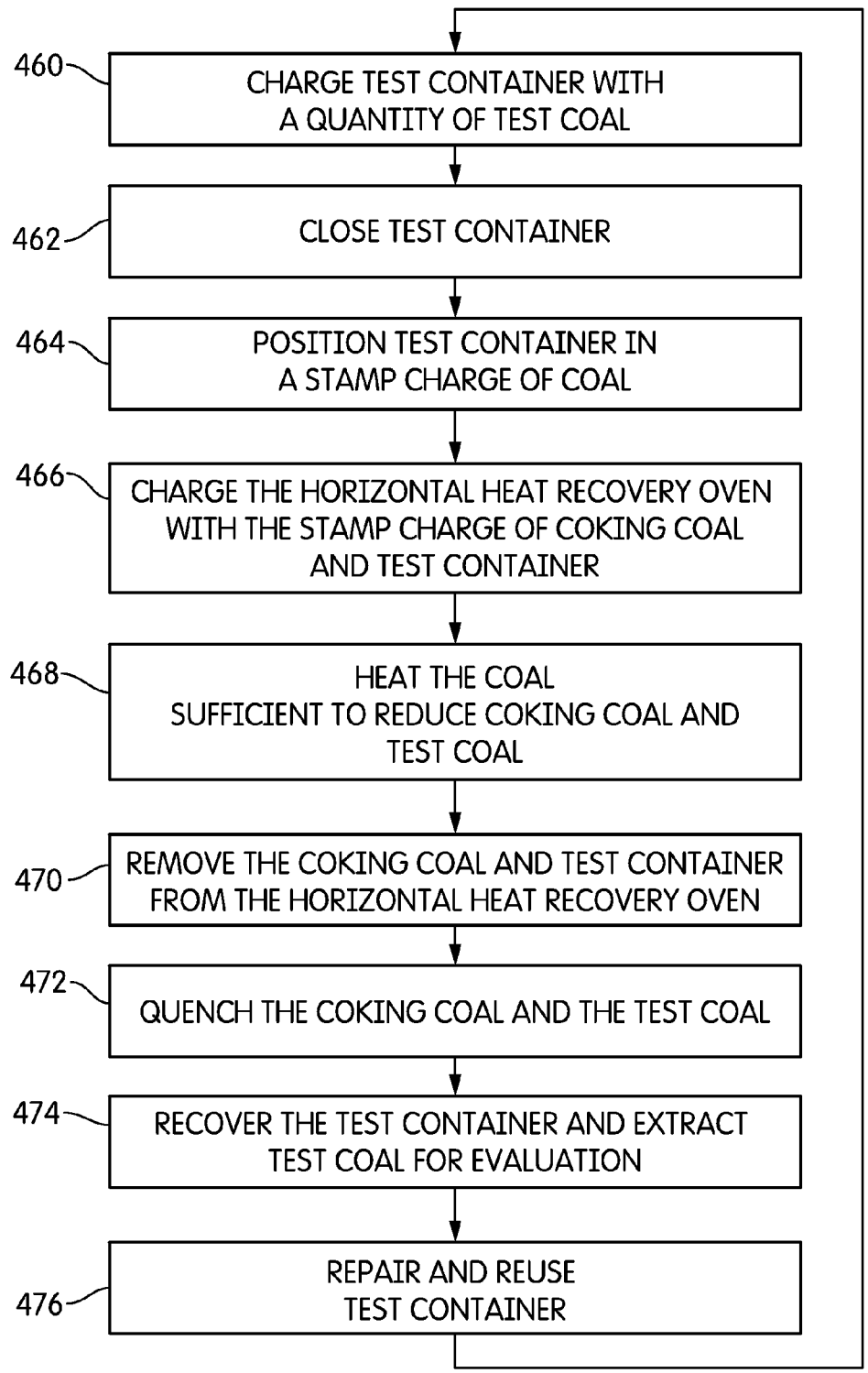
FIG. 14 is a schematic flow chart of a method for evaluating the coking properties of stamp charged coal in a coking oven using a reusable test container as described herein.

FIG. 14 provides a schematic flow chart of a method of using the test container during a conventional coke oven operation for a stamp charge of coke. The method begins with a charge of test coal being loaded 460 and in some cases packed into the test container 30 and then the test container is closed 462. The test container is positioned within a stamp charge of coal 64, typically placed within a recess formed in the stamp charge. As seen in FIG. 10, the test container 62 is ideally centrally located 464 within the stamp charge 170 and then placed 466 in the coking oven 14, ideally centrally located within the coking oven 14 with a supply of coking coal 16 is positioned around the test container to substantially surround all the side walls 34 of the container 30. Both the supply of coking coal 16 and the test coal inside the test container 30 are subjected to heat 468 from the coke oven 14 in a closely controlled atmosphere for a sufficient period of time to drive off the impurities and volatile matter converting at least a portion of the coal to coke. Once this conversion process is complete, the conventional converted coke, the test container and the test coal (now coke) contained therein, are removed from the coking oven 470. The converted coke and converted test coal are quenched 472 and then the test container 30 and converted test coal are recovered from the quenched material for evaluation and analysis of the coking capabilities of the test coal 474. The converted test coal is removed from the container and the test container 30 is then repaired, if necessary, and then reused 76 for a second testing operation of second quantity of test coal as described above.

Figure 11:
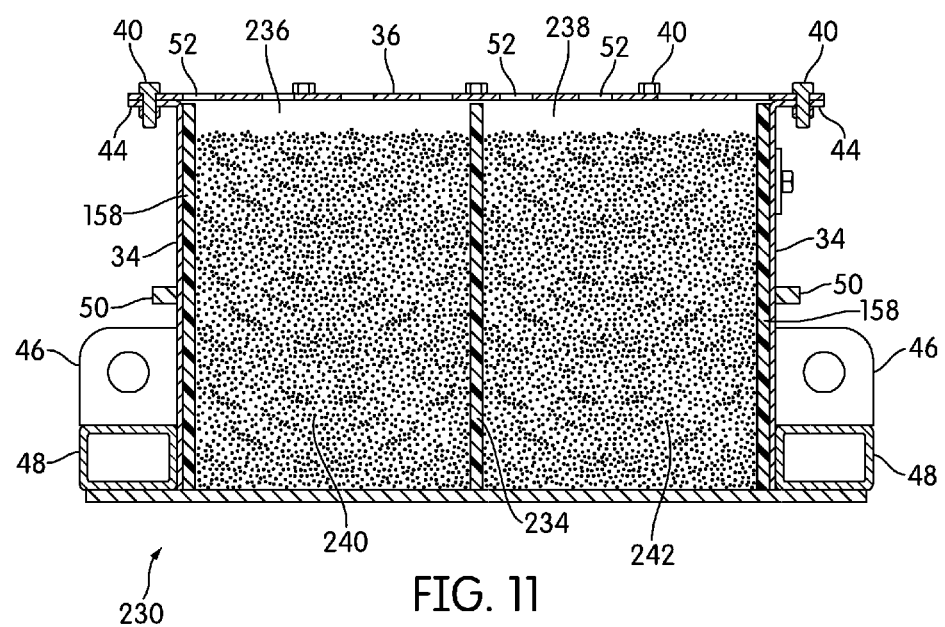
FIG. 11 is a sectional view of a reusable test container similar to the view of the reusable test container as seen in FIG. 9 showing a partition of the interior space of the container.

The testing method described in FIG. 7 begins with a charge of test coal being loaded 60 and packed into the test container 30 and then the test container is closed 62. This language suggests loading a single charge of test coal into the test container. However, it is envisioned that the hollow interior of the test container 30 could be subdivided into multiple compartments or cavities to allow for testing smaller quantities of different test coals. FIG. 11 shows a different test container 230 similar to the test containers seen in FIGS. 5 and 9. For ease of discussion, the same reference numerals will be used in FIG. 11 for elements which are common to FIGS. 5 and 9.

As seen in FIG. 11, the test container 230 incorporates the layers of thermally insulating material 158 on the inside of the container intermediate the side walls 134 and the test coal. However, the test container 230 also includes an divider element 234 which extends between opposite sides walls 34 of the test container 230 to create two different test spaces 236 and 238 into which a first test coal 240 and a second test coal 242, respectively, have been loaded. Preferably, the divider element 234 is formed from a material which will not react with or alter the coking process of the coal provided inside the container. One suitable product to use for the divider element is a thickness of the thermally insulating material 158 used to insulate the sidewalls 134 of the test container 130 discussed above in FIG. 9 and another suitable material is ceramic fiber board. Using this divided structure of the test container, smaller quantities of multiple different coal blends can be sampled for coking performance during a single coke oven production cycle. FIG. 11 shows the creation of two substantially evenly divided test spaces, but it is understood that any number of test spaces can be created within the test container 230 and the relative volume of the test spaces can be altered by movement of the divider element 234 within the test container 230.

Figure 12:
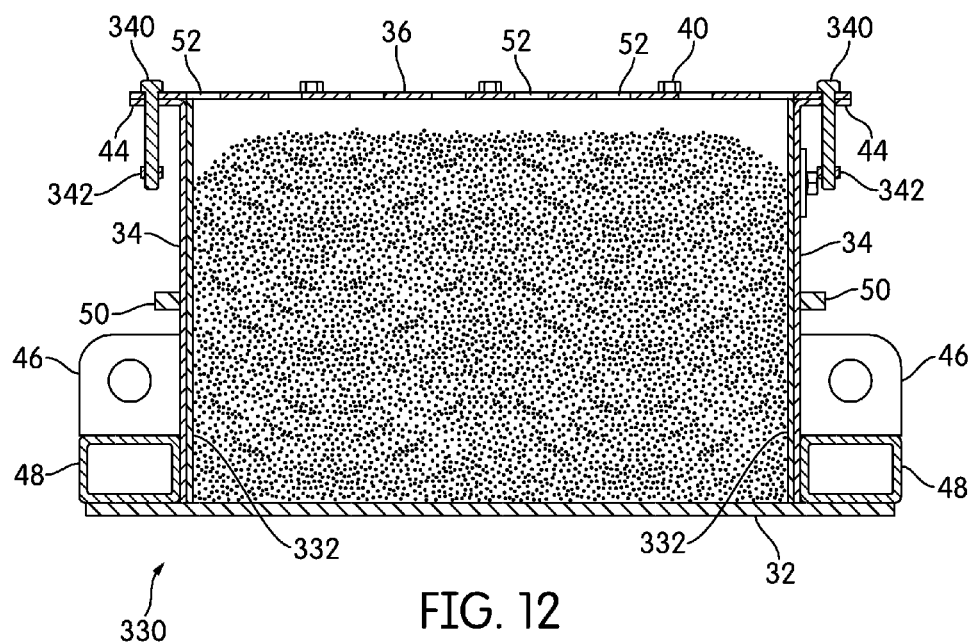
FIG. 12 is a sectional view of a reusable test container similar to the view of the reusable test container as seen in FIG. 11 showing an expandable in the unexpanded state.
Figure 13:
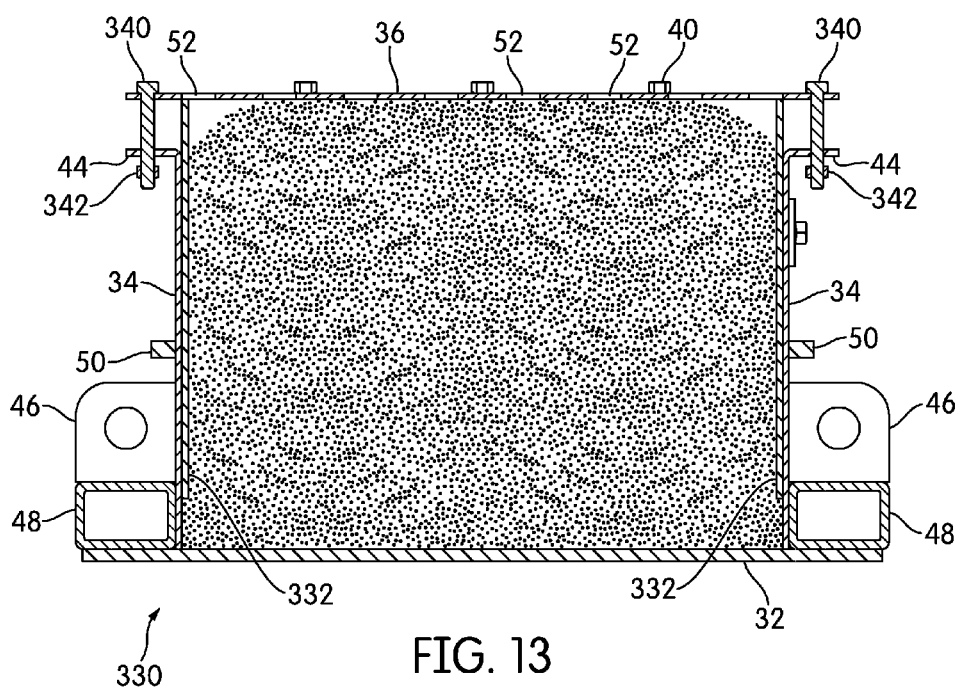
FIG. 13 is a sectional view of a reusable test container of FIG. 12 showing the expandable in the expanded state.

Converted coal to coke in a stamp charging operation can require slight modifications to the structure of the test container. In stamp charging operations, coals having lower quality coking performance can be mixed with higher quality coals to create a suitable blend. However, this mixing can result in a coal blend which will expand during the heating/reduction process. As seen in FIGS. 12 and 13, the test container can be easily modified to accommodate this expansion during the coke reducing process. As seen in FIG. 12, one or more sidewalls 332 project downward from the top 36 of the test container. The sidewalls 332 are designed to be telescopically received inside the sidewalls 34 of the test container, but the relative position of these walls to one another is not critical in that the sidewalls 332 can be telescopically received on the outside of the sidewalls 34 of the container. These sidewalls 332 and 34 cooperate with one another to act as guides for movement of the top 36 relative to the bottom 32 of the container 330. Means are provided to limit, contain or constrain the expansion of the top 36 relative to the bottom 32. Specifically, in FIGS. 12 and 13, elongated bolts 340 are mounted in top 36 and a cooperating flange 44 provided on the side wall 34. The bolt 340 passes through an aperture in the flange 44 and the diameter of the flange 44 aperture is slightly larger than the bolt 340 so that as the top 36 is forced away from the bottom 32 based upon the expansion of the coal blend (FIG. 13) the shaft of the elongated bolt 340 slides through the aperture in the flange 44 until the flange encounters the nut 342 or stop formed on the end of the elongated bolt 340. The elongated bolt 340 and cooperating flange 44 are just one example of a guide and limit on the movement of the top 36 relative to the bottom 36 of the test container 330. Other examples include a projection formed on one of the side walls and a complementary groove or slot formed on the other side wall which allows movement of the top 36 relative to the bottom 32. Similarly, rails or guides can be used to both guide and control or limit movement of the top 36 relative to the bottom 32.

Figure 15:
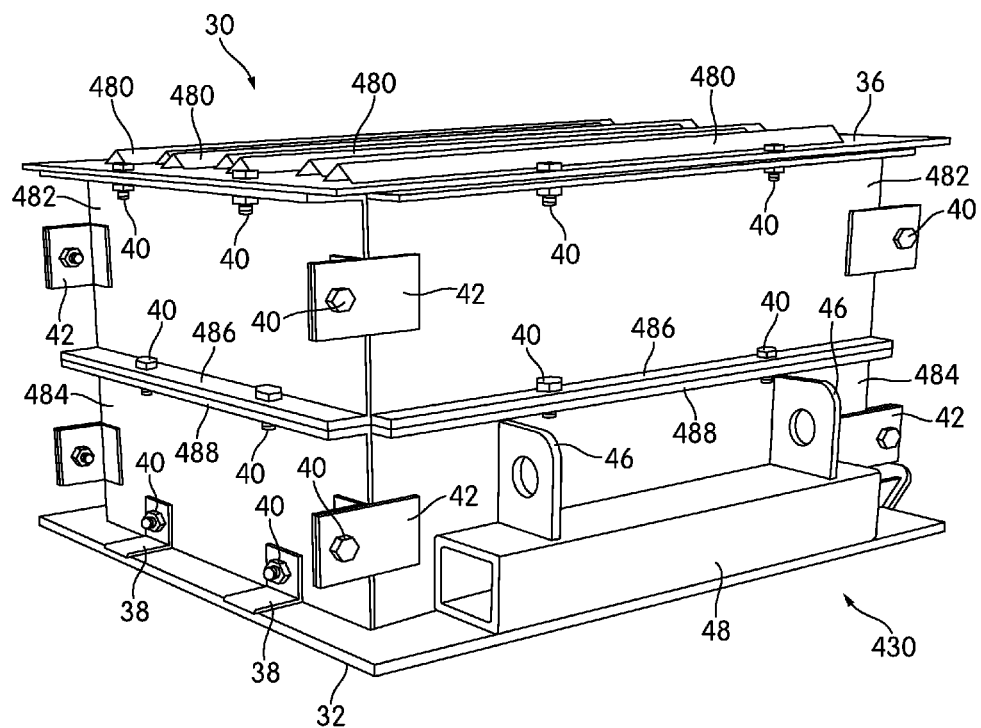
FIG. 15 is a perspective view of another variation on reusable test container similar to that seen in FIG. 2.

FIG. 15 shows yet another different test container 430 similar to the test container seen in FIG. 2. For ease of discussion, the same reference numerals will be used in FIG. 15 for elements which are common to FIG. 2. The test container 430 seen incorporates additional elements from the previous test containers. For example, in some applications, it can be important to ensure that none of the conventional coal which is loaded around the test container during the coking operation inadvertently enters the test container. So, in some cases, it can be important to ensure that the surrounding coal or other impurities cannot easily enter the test container 430 while still incorporating apertures on the top 36 to allow for the passing of gases and fluids into and out of the test container 430 during the coking and quenching steps. One way to accomplish this goal is to mount one or more cover members to the top 36 of the test container. As seen in FIG. 15, cover members or channels 480 formed of steel are welded to the top 36 of the test container in such a manner to cover the apertures in the top 36, but still allow the free movement of gases and fluids through the apertures and channels 480. With this structure, the volatile gases expelled from the coal during the coking operation can escape the test container 480 and quenching fluid and steam can enter and exit the test container 430. However, coal which is loaded on top of the test container 430 during the charging step, will not inadvertently enter the test container 430. An alternative to the multiple channels would be to mount to the top 36 in a spaced relation a cover member or plate also having a plurality of apertures which do not align with the apertures formed in the top 36. With this structure, gases and fluid could again pass through the apertures in the top 36, pass through the space between the top 36 and the plate and then pass through the apertures formed in the plate.

Another option integrated into the test container 430 seen in FIG. 15 related to the side walls. In FIG. 2, four side walls 34 were mounted to one another to create the fours sided box. In the test container seen in FIG. 15, each side wall is constructed from a plurality of elements, specifically an upper side wall member 482 and a lower side wall member 484. The upper and lower side wall members 482, 484 are mounted to the top 36 and bottom 32 walls of the box in the same manner as described above. However, the side wall members each incorporate a laterally extending flange, 486 and 488, respectively. The flanges are mounted, preferably welded, to the side walls and then mounted to one another by conventional bolts and nuts 40. With this structure, it can be easier to repair a portion of the side wall of the box. Testing has shown that the upper edges of the side walls of the box tend to fail first. Therefore, by creating a segmented side wall, the lifespan of the box can be dramatically increased. Testing has shown that the total lifespan of the test container can be doubled by providing a simple means such as the segmented sidewall for permitting easy repair of portions of the test container.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

It should be noted that the orientation of various elements may differ according to other exemplary embodiments, and that such variations are intended to be encompassed by the present disclosure.

It is also important to note that the constructions and arrangements of the test container and processes described in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

What is claimed is:

1. A method for evaluating the coking properties of coal produced in a coking oven comprising:
    positioning a quantity of test coal into an interior chamber of a test container having a plurality of apertures that penetrate at least one wall of the test container; the apertures being positioned in open communication with the interior chamber and shaped to allow the passage of fluids into, and from within, the interior chamber through the at least one wall;
    positioning the test container in a horizontal heat recovery coking oven and charging the horizontal heat recovery coking oven with a supply of coking coal;
    heating the test coal, test container and supply of coking coal to reduce at least a portion of the quantity of test coal to coke; and
    removing the test container and supply of coking coal from the horizontal heat recovery coking oven;
    recovering the test container for re-use; and
    recovering the quantity of test coal from the test container for evaluation of the coking properties of the test coal.

2. The method of claim 1 wherein the test container is formed, a least in part, from materials selected from the group of steel, ceramic, and refractory materials.

3. The method of claim 1 and further comprising the step of compacting the test coal inside the test container prior to positioning the test container in the horizontal heat recovery oven.

4. The method of claim 1 and further comprising the step of positioning the test container in the horizontal heat recovery oven before the horizontal heat recovery oven is fully charged with the supply of coking coal so that at least a portion of the supply of coking coal substantially surrounds the test container.

5. The method of claim 4 wherein the test container is placed in the horizontal heat recovery oven before the supply of coking coal and then the supply of coking coal is placed in the horizontal heat recovery oven to substantially surround the test container.

6. The method of claim 4 wherein the test container comprises a bottom wall, a top wall, and at least one side wall extending between the bottom and top walls and the supply of coking coal substantially surrounds the at least one side wall inside the horizontal heat recovery oven prior to the reduction of at least a portion of the quantity of test coal and the supply of coking coal.

7. The method of claim 6 wherein at least a portion of the supply of coking coal substantially surrounds the top wall of the test container inside the horizontal heat recovery oven prior to the reduction of at least a portion of the quantity of test coal and the supply of coking coal.

8. The method of claim 6 wherein the test container is constructed so that at least one of the top, bottom and at least one side walls is moveable relative to the at least one of the other of the top, bottom and at least one side walls to accommodate for expansion of quantity of test coal during the reducing process.

9. The method of claim 1 and further comprising the step of positioning thermally insulating material inside the test container intermediate at least a portion of the test container and the quantity of test coal.

10. The method of claim 9 wherein the test container comprises a bottom wall, a top wall, at least one side wall extending between the bottom and top walls and the insulating material is positioned intermediate the test coal and the at least one side of the test container.

11. The method of claim 1 wherein the supply of coking coal comprises a substantially solid charge and further comprising the steps of forming a recess in the substantially solid charge sufficient to receive at least a portion of the test container and positioning the test container in the recess prior to the reduction of at least a portion of the quantity of test coal and the supply of coking coal.

12. The method of claim 11 wherein the test container comprises a bottom wall, a top wall, and at least one side wall member extending between the bottom and top walls and the supply of coking coal substantially surrounds the at least one side wall inside the horizontal heat recovery oven prior to the reduction of at least a portion of the quantity of test coal and the supply of coking coal.

13. The method of claim 1 wherein the test container comprises a bottom wall, a top wall, and at least one side wall member extending between the bottom and top walls and further comprises the step of removing the top wall of the test container to accommodate recovering the quantity of test coal from the test container for evaluation of the coking properties of the test coal.

14. The method of claim 1 and further comprising the steps of reusing the test container by providing a second quantity of test coal for evaluation;
   positioning the second quantity of test coal into the test container;
   positioning the test container in a coking oven and charging the coking oven with a second supply of coking coal;
   heating the second quantity of test coal, test container and second supply of coking coal to reduce at least a portion of the second quantity of test coal and the second supply of coking coal to coke; and
   removing the test container and second supply of coking coal from the coking oven; and
   recovering the second quantity of test coal from the test container for evaluation of the coking properties of the second quantity of test coal.

15. The method of claim 14 wherein the test container comprises a bottom wall, a top wall, and at least one side wall extending between the bottom and top walls and further comprises the step of removing the top wall of the test container to accommodate recovering the second quantity of test coal from the test container for evaluation of the coking properties of the second quantity of test coal.

16. The method of claim 14 and further comprising the steps of subdividing the interior chamber of the test container with a dividing element to create at least two separate test spaces within the test container that are each defined by at least one wall of the test container and a divider element and adapted to receive one or more supplies of coal for testing.

17. The method of claim 1 and further comprising the steps of subdividing the interior chamber of the test container with a dividing element to create at least two separate test spaces within the test container that are each defined by at least one wall of the test container and a divider element and adapted to receive one or more supplies of coal for testing.

18. The method of claim 1 wherein at least one of the plurality of apertures penetrates a top wall of the test container and allows the passage of fluids into, and from within, the interior chamber through the top wall.

19. The method of claim 1 wherein at least one of the plurality of apertures penetrates a side wall of the test container and allows the passage of fluids into, and from within, the interior chamber through the side wall.

20. The method of claim 1 wherein at least one of the plurality of apertures penetrates a bottom wall of the test container and allows the passage of fluids into, and from within, the interior chamber through the bottom wall.

21. The method of claim 1 wherein at least some of the plurality of apertures penetrate a top wall and at least one side wall of the test container and allows the passage of fluids into, and from within, the interior chamber through the top wall and at least one side wall.

22. The method of claim 1 wherein the plurality of apertures penetrate a top wall, a bottom wall, and at least one side wall of the test container and allows the passage of fluids into, and from within, the interior chamber through the top wall, bottom wall, and at least one side wall.

23. A method for evaluating the coking properties of coal in a horizontal heat recovery coking oven comprising:
   positioning a first quantity of test coal into an interior chamber of a reusable test container having a plurality of apertures that penetrate at least one wall of the test container; the apertures being positioned in open communication with the interior chamber and shaped to allow the passage of fluids into, and from within, the interior chamber through the at least one wall; the reusable test container being formed from a material which will not be consumed during the reduction process;
   positioning the test container in a horizontal heat recovery coking oven;
   providing a charge of coking coal in the horizontal heat recovery coking oven to surround, at least in part, the test container;
   heating the first quantity of test coal, the test container and coking coal to reduce at least a portion of the quantity of test coal and the coking coal into coke;
   removing the coke and the test container from the horizontal heat recovery coking oven;
   recovering the reduced coke from inside the test container for testing and evaluation;
   providing a second quantity of test coal for evaluation;
   positioning at least a portion of the second quantity of test coal into the interior chamber of the test container;
   positioning the test container in a horizontal heat recovery coking oven;
   providing a charge of coking coal in the horizontal heat recovery coking oven to surround, at least in part, the test container;
   heating the second quantity of test coal, the test container and coking coal to reduce at least a portion of the second quantity of test coal and the coking coal into coke;
   removing the coke and the test container from the horizontal heat recovery coking oven; and
   recovering the reduced coke from inside the test container for testing and evaluation.

24. A method for evaluating the coking properties of coal produced in a coking oven comprising:
   providing a quantity of test coal for evaluation;
   providing a test container which is adapted to receive the quantity of test coal and is gas permeable;
   inserting a barrier liner into the test container to reduce the loss of test coal from the test container;
   positioning the quantity of test coal into the test container;
   positioning the test container in a horizontal heat recovery coking oven and charging the horizontal heat recovery coking oven with a supply of coking coal;
   heating the test coal, test container and supply of coking coal to reduce at least a portion of the quantity of test coal to coke; and
   removing the test container and supply of coking coal from the horizontal heat recovery coking oven;
   recovering the test container for re-use; and
   recovering the quantity of test coal from the test container for evaluation of the coking properties of the test coal.

25. The method of claim 24 wherein the barrier liner is consumed during the steps of heating the test container.

* * * * *

UNITED STATES PATENT AND TRADEMARK OFFICE
CERTIFICATE OF CORRECTION

| | |
|---|---|
| PATENT NO. | : 9,169,439 B2 |
| APPLICATION NO. | : 13/598394 |
| DATED | : October 27, 2015 |
| INVENTOR(S) | : Jacob P. Sarpen et al. |

It is certified that error appears in the above-identified patent and that said Letters Patent is hereby corrected as shown below:

IN THE CLAIMS

In column 10, line 10, in claim 2, delete "a least" and insert -- at least --, therefor.

In column 10, line 63, in claim 12, before "extending" delete "member".

In column 11, line 3, in claim 13, before "extending" delete "member".

Signed and Sealed this
Twenty-ninth Day of March, 2016

Michelle K. Lee
*Director of the United States Patent and Trademark Office*